US00PP23768P3

(12) United States Plant Patent
Scheffers

(10) Patent No.: US PP23,768 P3
(45) Date of Patent: Jul. 23, 2013

(54) ***EUPHORBIA* PLANT NAMED 'DB200801'**

(50) Latin Name: *Euphorbia geroldii*
Varietal Denomination: DB200801

(75) Inventor: Ruud Scheffers, Honselersdijk (NL)

(73) Assignee: Dragontree Beheer BV (NL)

( * ) Notice: Subject to any disclaimer, the term of this patent is extended or adjusted under 35 U.S.C. 154(b) by 25 days.

(21) Appl. No.: 13/136,114

(22) Filed: Jul. 22, 2011

(65) Prior Publication Data

US 2013/0025012 P1 Jan. 24, 2013

(51) Int. Cl.
*A01H 5/00* (2006.01)

(52) U.S. Cl.
USPC ..... Plt./302

(58) Field of Classification Search
USPC ..... Plt./302
See application file for complete search history.

*Primary Examiner* — Susan McCormick Ewoldt
(74) *Attorney, Agent, or Firm* — Cassandra Bright

(57) ABSTRACT

A new and distinct *Euphorbia* cultivar named 'DB200801' is disclosed, characterized by continuous flowering that begins as soon as a rooted cutting is planted. Flowers occur two per flowering branch. The near variety is a *Euphorbia,* typically used for indoor or outdoor ornamental purposes.

1 Drawing Sheet

Latin name of the genus and species: *Euphorbia geroldii.*
Variety denomination: 'DB200801'.

BACKGROUND OF THE INVENTION

The new cultivar was discovered as a naturally occurring, spontaneous branch mutation, among a experimental planting of *Euphorbia geroldii* unpatented, unnamed cultivar. 'DB200801' was discovered by the inventor, Ruud Scheffers, a citizen of the Netherlands in May of 2007, at a commercial greenhouse in Honselersdijk, The Netherlands.

Approximately 2 months after discovery of the interesting mutation, the inventor first propagated the new variety by vegetative cuttings. After reproducing 'DB200801' by cuttings, the inventor observed the plants started flowering immediately the cuttings were planted. Subsequent reproduction of 'DB200801' by cuttings has shown that the unique features of this cultivar are stable and reproduced true to type through several generations. The inventor filed an application for Plant Breeders Right in the Netherlands Apr. 2, 2010, with application number EGL1. No rights have been granted at the time of filing this application, and no sales have taken place. All plants of 'DB200801' have been kept in the inventor's greenhouse, with restricted access, and no access to the variety has been allowed to third parties or the public. At the time of filing of this application with the USPTO, there have been no advertising or offers for sale related to 'DB200801'.

SUMMARY OF THE INVENTION

The cultivar 'DB200801' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DB200801' These characteristics in combination distinguish 'DB200801' as a new and distinct *Euphorbia* cultivar:

1. Plants begin flowering immediately after planting a vegetative cutting.
2. Two flowers per flowering branch.
3. Continuous flowering.

COMPARISON TO PARENT

Plants of the new cultivar 'DB200801' are similar to plants of the parent; *Euphorbia geroldii* in most horticultural characteristics, however, plants of the new cultivar 'DB200801' produce foliage with a different shape, and have an overall more compact plant habit. Additionally, the new variety produces glossier foliage than the parent.

COMMERCIAL COMPARISON

The most similar commercial comparison is the parent variety.

BRIEF DESCRIPTION OF THE PHOTOGRAPH

The accompanying photograph in FIG. 1 illustrates in full color a typical plant of 'DB200801' grown in a greenhouse in Honselerdijk, the Netherlands.

This plant is approximately 6 months old, shown in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001, except where general terms of ordinary dictionary significance are used. The following observations and measurements describe 'DB200801' plants grown in a commercial greenhouse in the Netherlands, from February of 2010 through October of 2010. Temperatures were approximately 20° C. at night and 20° C. during the day. Measurements and numerical values represent averages of typical plant types. No growth regulators or special treatments were used.

Botanical classification: *Euphorbia geroldii* 'DB200801'.

PROPAGATION

Time to initiate roots: Approximately 10 days at 20° C.

Root description: Very dense and freely branching, moderately fine, slightly fibrous, non-fleshy, colored near RHS Brown 199D.

PLANT

Growth habit: Upright tender perennial.

Plant shape: Inverted triangle.

Height: Approximately 245 cm in a 12 cm pot.

Plant spread: Approximately 36 cm.

Growth rate: Moderate.

Branching characteristics: Free branching.

Length of primary lateral branches: Approximately 13.8 cm.

Quantity of primary lateral branches: Average 18.

Characteristics of primary lateral branches:

*Diameter.*—0.3 cm.

*Color.*—RHS Yellow-Green 148A. Older stems near Greyed-Green 198A, tinged RHS Brown 201C.

*Texture.*—Smooth, moderately glossy.

*Strength.*—Moderately strong.

Internode length: Average 2.6 cm.

Age of plant described: Approximately 6 months from a rooted cutting.

FOLIAGE

Leaf:

*Quantity per branch.*—Average 8.

*Leaf arrangement.*—Alternate, single.

*Average leaf length.*—Approximately 8.6 cm.

*Average leaf width.*—Approximately 3.7 cm.

*Shape.*—Obovate to narrow obovate.

*Apex.*—Acute.

*Base.*—Long attenuate.

*Aspect.*—Slight reflex back.

*Margin.*—Entire, wavy.

*Texture of top surface.*—Smooth.

*Texture of bottom surface.*—Smooth.

*Appearance of top surface.*—Glossy.

*Appearance of bottom surface.*—Glossy.

*Pubescence.*—No pubescence.

*Color.*—Young foliage upper side: Near RHS Green 143A, but darker. Young foliage under side: Near RHS Yellow-Green 144B. Mature foliage upper side: Near RHS Green 139A, but much darker. Mature foliage under side: Near RHS Yellow-Green 144A and also 146B.

*Venation.*—Type: Pinnate. Venation coloration upper side: Near RHS Green 137A. Venation coloration under side: Near RHS Yellow-Green 148A.

Leaf petiole:

*Length.*—Approximately 1.1 cm.

*Width.*—Approximately 0.15 cm.

*Color.*—Upper side: Near RHS Red 47C.

*Strength.*—Strong.

Other foliage characteristics: Very resistant to mechanical and environmental stress. White latex produced when stems or leaves damaged.

FLOWER

Arrangement: Axillary, simple umbel, flowers in pairs. Approximately 24 flowers and buds per plant.

Natural flowering season: Continuous, non seasonal.

Flower longevity on plant: Approximately 1 week.

Rate of opening: Approximately 1 week after bud stage.

Persistent or self-cleaning: Self-Cleaning.

Fragrance: None.

Bud:

*Shape.*—Ovate.

*Length.*—0.3 cm.

*Diameter.*—0.1 cm.

*Color.*—Near RHS Yellow-Green 144C.

Inflorescence size:

*Diameter.*—Average 1.5 cm.

*Depth.*—Average 2.4 cm.

Detailed inflorescence description: Staminate flowers consisting of anthers only, no petals, no sepals, each "flower" is supported by 5 conspicuous glands, an average of 5 individual (staminate) flowers is supported by two conspicuous bracts. Each individual staminate flower is supported by one gland, kidney-shaped, average length: 1 mm, average width 2 mm, coloured yellow-orange; 17B. Flowers are grouped in five, supported by two conspicuous bracts, shaped reniform, top rounded, base reniform, average length: 1.0 cm, average width: 1.4 cm, texture is glabrous. Upper side of immature bract coloured near RHS Red 39A, under side lighter; 39B, Upper side of mature bract red; 41B, under side lighter; 41C.

Flower size:

*Diameter.*—Average 0.2 cm.

*Depth.*—Average 0.2 cm.

*Other.*—Flowers minute, of indeterminate color.

Peduncles:

*Length.*—2.0 cm.

*Diameter.*—0.15 cm.

*Angle.*—About 35° to the lateral branch.

*Strength.*—Moderately strong.

*Texture.*—Smooth, slightly glossy.

*Color.*—Near RHS Yellow-Green 144B, flushed RHS Greyed-Red 179C.

Pedicels:

*Length.*—Average 0.6 cm.

*Diameter.*—0.15 cm.

*Angle.*—About 30° to the lateral branch.

*Strength.*—Moderately strong.

*Texture.*—Smooth, slightly glossy.

*Color.*—Near RHS Yellow-Green 144C, flushed RHS Greyed-Red 179B.

REPRODUCTIVE ORGANS

Stamens:

*Number.*—1 stamen with 2 anthers.

Anthers:

*Shape.*—Basifixed, rounded.

*Length.*—Approximately 0.5 mm., filament approximately 1.5 mm.

*Color.*—Near RHS Yellow-Green 153C.

*Pollen.*—Color: Near RHS Yellow-Green 153D. Quantity: Scant.

Pistil:

*Number.*—Average: 1, with 3 stigmas.

*Length.*—3 mm.

*Style.*—Length: 2.9 mm. Color: Near RHS Yellow-Green 150D.

*Stigma.*—Shape: Cleft (2-parted). Color: Near RHS Brown 200C. Ovary Color: Near RHS Yellow-Green 150D.

OTHER CHARACTERISTICS

Seed production: Not observed to date.

Disease resistance: Neither resistance nor susceptibility to diseases or pests has been observed in this variety.

Temperature tolerance: Low temperature tolerance to at least 5° C., high temperatures to at least 40° C.

Drought tolerance: Unknown.

What is claimed is:

1. A new and distinct cultivar of *Euphorbia* plant named 'DB200801' as herein illustrated and described.

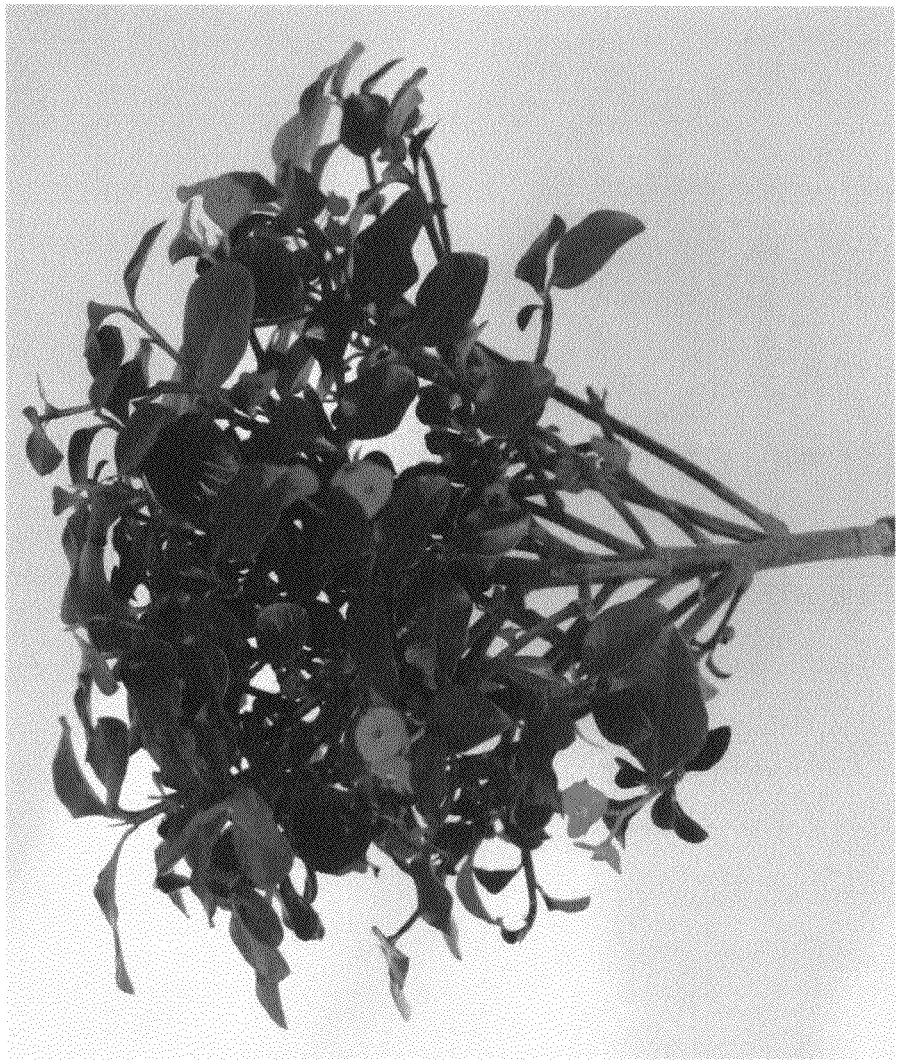

* * * * *